US011779251B2

(12) United States Patent
Alford et al.

(10) Patent No.: US 11,779,251 B2
(45) Date of Patent: *Oct. 10, 2023

(54) SYSTEMS AND METHODS FOR RECORDING NEURAL ACTIVITY

(71) Applicant: HI LLC, Los Angeles, CA (US)

(72) Inventors: Jamu Alford, Lake Arrowhead, CA (US); Micah Ledbetter, Sunnyvale, CA (US); Ricardo Jiménez-Martínez, Culver City, CA (US); Ethan Pratt, Santa Clara, CA (US)

(73) Assignee: HI LLC, Los Angeles, CA (US)

( * ) Notice: Subject to any disclaimer, the term of this patent is extended or adjusted under 35 U.S.C. 154(b) by 346 days.

This patent is subject to a terminal disclaimer.

(21) Appl. No.: 17/328,235

(22) Filed: May 24, 2021

(65) Prior Publication Data
US 2021/0369166 A1 Dec. 2, 2021

Related U.S. Application Data

(60) Provisional application No. 63/076,015, filed on Sep. 9, 2020, provisional application No. 63/031,469, filed on May 28, 2020.

(51) Int. Cl.
*A61B 5/245* (2021.01)
*A61B 5/00* (2006.01)
*G01R 33/26* (2006.01)

(52) U.S. Cl.
CPC .......... *A61B 5/245* (2021.01); *A61B 5/6803* (2013.01); *G01R 33/26* (2013.01); *A61B 2562/182* (2013.01)

(58) Field of Classification Search
CPC ..... A61B 5/245; A61B 5/6803; A61B 5/6889; A61B 5/6814; A61B 5/6888;
(Continued)

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

CN 104730484 6/2015
CN 107562188 1/2018
(Continued)

OTHER PUBLICATIONS

Wang, Qingmeng, et al. "A high performance static magnetic shielded room for detecting biomagnetic nanoparticles." 2010 Asia-Pacific International Symposium on Electromagnetic Compatibility. IEEE, 2010. (Year: 2010).*
(Continued)

*Primary Examiner* — Sean D Mattson
(74) *Attorney, Agent, or Firm* — Branch Partners PLLC; Bruce E. Black

(57) ABSTRACT

A shielding arrangement for a magnetoencephalography (MEG) system includes a passively shielded enclosure having a plurality of walls defining the passively shielded enclosure, each of the plurality of walls including passive magnetic shielding material to reduce an ambient background magnetic field within the passively shielded enclosure; a vestibular wall extending from a first vertical wall to define, and at least partially separate, a vestibular area of the passively shielded enclosure adjacent the doorway and a user area of the passively shielded enclosure; and active shield coils distributed within the passively shielded enclosure and configured to further reduce the ambient background magnetic field within the user area of the passively shielded enclosure.

18 Claims, 7 Drawing Sheets

(58) Field of Classification Search
CPC ............ A61B 5/0046; A61B 2562/182; G01R 33/26; G01R 33/0076; G01R 33/0094; G01R 33/032
See application file for complete search history.

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 5/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2008/0294386 A1* | 11/2008 | Taulu .................... A61B 5/245 702/191 |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0197838 A1* | 8/2013 | Simola ................... A61B 5/055 702/65 |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0219732 A1* | 8/2015 | Diamond ............... G01R 33/16 324/201 |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1 | 10/2016 | Ueno |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorensen et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0368191 A1* | 12/2019 | Shibuya ............... H05K 9/0003 |
| 2019/0391213 A1 | 12/2019 | Alford |
| 2020/0025844 A1 | 1/2020 | Alford et al. |
| 2020/0056263 A1 | 2/2020 | Bhattacharyya et al. |
| 2020/0057115 A1 | 2/2020 | Jiménez-Martínez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0109481 A1 | 4/2020 | Sobek et al. |
| 2020/0123416 A1 | 4/2020 | Bhattacharyya et al. |
| 2020/0191883 A1 | 6/2020 | Bhattacharyya et al. |

(56) References Cited

U.S. PATENT DOCUMENTS

| | | |
|---|---|---|
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0011094 A1 | 1/2021 | Bednarke |
| 2021/0015385 A1 | 1/2021 | Katnani et al. |
| 2021/0015427 A1 | 1/2021 | Shah et al. |
| 2021/0041512 A1 | 2/2021 | Pratt et al. |
| 2021/0041513 A1 | 2/2021 | Mohseni |
| 2021/0063510 A1 | 3/2021 | Ledbetter |
| 2021/0369165 A1* | 12/2021 | Alford ............... G01R 33/0076 |

FOREIGN PATENT DOCUMENTS

| | | |
|---|---|---|
| CN | 110742607 | 2/2020 |
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Holmes, Niall, et al. "A bi-planar coil system for nulling background magnetic fields in scalp mounted magnetoencephalography." Neuroimage 181 (2018): 760-774. (Year: 2018).*

Sullivan, Go W., et al. "A magnetic shielded room designed for magnetoencephalography." Review of scientific instruments 60.4 (1989): 765-770. (Year: 1989).*

International Search Report and Written Opinion for PCT Application No. PCT/US2021/033861 dated Sep. 1, 2021.

Rodriguez Vince: "On the design of door-less access passages to shielded enclosures", 2017 Antenna Measurement Techniques Association Symposium (AMTA), AMTA, Oct. 15, 2017 (Oct. 15, 2017), pp. 1-6.

Smit Mobile Equipment B.V.: "Mobile MRI", Dec. 19, 2016 (Dec. 19, 2016), Retrieved from the Internet: URL:https://web.archive.org/web/20161219022429/https://smit.one/products/mobile%20mri.html.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K.L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Griffith, W.C., Knappe, S. and Kitching, J., "Femtotesla atomic magnetometry in a microfabricated vapor cell." Optics express 18, (26), 27167-27172 (2010).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multi-channel magnetoencephalography." NeuroImage, 199, 598-608 (2019).

Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).

Iivanainen, J., Stenroos, M. and Parkkonen, L., "Measuring MEG closer to the brain: Performance of on-scalp sensor arrays." NeuroImage 147, 542-553 (2017).

Kitching, J., Knappe, S., Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).

(56) References Cited

OTHER PUBLICATIONS

Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.
Zhang Xin et al: "Detection and analysis of MEG signals in occipital region with double channel OPM sensors", Journal of Neuroscience Methods, Elsevier Science Publisher B. V., Amsterdam, NL, vol. 346, Sep. 17, 2020 (Sep. 17, 2020).
Hill RM, Boto E, Holmes N, et al. A tool for functional brain imaging with lifespan compliance [published correction appears in Nat Commun. Dec. 4, 2019;10(1):5628]. Nat Commun. 2019; 10(1):4785. Published Nov. 5, 2019. doi:10.1038/s41467-019-12486-x.
Zetter, R., Iivanainen, J. & Parkkonen, L. Optical Co-registration of MRI and On-scalp MEG. Sci Rep 9, 5490 (2019). https://doi.org/10.1038/s41598-019-41763-4.
Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.
Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.
V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.
Holmes, N., Tierney, T.M., Leggett, J. et al. Balanced, bi-planar magnetic field and field gradient coils for field compensation in wearable magnetoencephalography. Sci Rep 9, 14196 (2019).
N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.
J. M. Leger et. al., In-flight performance of the Absolute Scalar Magnetometer vector mode on board the Swarm satellites, Earth, Planets, and Space (2015) 67:57.
Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.
Gravrand, O., Khokhlov, A., & JL, L. M. (2001). On the calibration of a vectorial 4He pumped magnetometer. Earth, planets and space , 53 (10), 949-958.
Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.
Vrba J, Robinson SE. Signal processing in magnetoencephalography. Methods. 2001;25(2):249-271. doi:10.1006/meth.2001.1238.
Uusitalo M and Ilmoniemi R., 1997, Signal-space projection method for separating MEG or EEG into components. Med. Biol. Comput. (35) 135-140.
Taulu S and Kajola M., 2005, Presentation of electromagnetic multichannel data: the signal space separation method. J. Appl. Phys. (97) 124905 (2005).
Taulu S, Simola J and Kajola M., 2005, Applications of the signal space separation method. IEEE Trans. Signal Process. (53) 3359-3372 (2005).
Taulu S, Simola J., 2006, Spatiotemporal signal space separation method for rejecting nearby interference in MEG measurements. Phys. Med. Biol. (51) 1759-1768 (2006).
Johnson, et al., Magnetoencephalography with a two-color pump-probe, fiber-coupled atomic magnetometer, Applied Physics Letters 97, 243703 2010.
Zhang, et al., Magnetoencephalography using a compact multichannel atomic magnetometer with pump-probe configuration, AIP Advances 8, 125028 (2018).
Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (p. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.
Pasquarelli, A, M De Melis, Laura Marzetti, Hans-Peter Müller, and S N Erné. "Calibration of a Vector-MEG Helmet System." Neurology & Clinical Neurophysiology: NCN 2004 (Feb. 1, 2004): 94.
Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS ONE 13, No. 5 (May 10, 2018): e0191111.
Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

(56) References Cited

OTHER PUBLICATIONS

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con)volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

(56) References Cited

OTHER PUBLICATIONS

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

\* cited by examiner

Magnitude of ambient field (nanoTesla)

SYSTEMS AND METHODS FOR RECORDING NEURAL ACTIVITY

CROSS-REFERENCE TO RELATED APPLICATIONS

This application claims the benefit of U.S. Provisional Patent Application Ser. Nos. 63/031,469, filed May 28, 2020; and 63/076,015, filed Sep. 9, 2020, both of which are incorporated herein by reference in their entireties.

FIELD

The present disclosure is directed to the area of magnetic field measurement systems including systems for magnetoencephalography (MEG). The present disclosure is also directed to magnetic field measurement systems and methods for suppressing background or interfering magnetic fields.

BACKGROUND

In the nervous system, neurons propagate signals via action potentials. These are brief electric currents which flow down the length of a neuron causing chemical transmitters to be released at a synapse. The time-varying electrical currents within an ensemble of neurons generate a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices.

BRIEF SUMMARY

One embodiment is a shielding arrangement for a magnetoencephalography (MEG) system that includes a passively shielded enclosure having a plurality of walls defining the passively shielded enclosure, each of the plurality of walls including passive magnetic shielding material to reduce an ambient background magnetic field within the passively shielded enclosure, where the plurality of walls includes a floor, a ceiling, and a first vertical wall having an open doorway without a door for entering or exiting into the passively shielded enclosure; a vestibular wall extending from the first vertical wall to define, and at least partially separate, a vestibular area of the passively shielded enclosure adjacent the doorway and a user area of the passively shielded enclosure; and active shield coils distributed within the passively shielded enclosure and configured to further reduce the ambient background magnetic field within the user area of the passively shielded enclosure.

In at least some embodiments, at least one of the active shield coils is configured for attachment to at least one of the walls of the passively shielded enclosure. In at least some embodiments, all of the active shield coils are configured for attachment to the walls of the passively shielded enclosure. In at least some embodiments, at least one of the active shield coils is configured for free-standing in the passively shielded enclosure.

In at least some embodiments, the plurality of walls includes a plurality of vertical walls including the first vertical wall, wherein the active shield coils are configured for attachment to the vertical walls. In at least some embodiments, the shielding arrangement further includes an active shield controller coupleable to the active shield coils, wherein the active shield controller is configured to provide a plurality of independent channels with each of the active shield coils coupled to any one of the independent channels. In at least some embodiments, the active shield coils include at least thirty active shield coils.

In at least some embodiments, the vestibular wall extends between the floor and the ceiling. In at least some embodiments, the vestibular wall extends at least halfway between the first vertical wall and the other of the walls. In at least some embodiments, the shielding arrangement further includes a mobile platform, wherein the passively shielded enclosure is mounted on the mobile platform.

Another embodiment is a magnetoencephalography (MEG) system that includes a passively shielded enclosure having a plurality of walls defining the passively shielded enclosure, each of the plurality of walls including passive magnetic shielding material to reduce an ambient background magnetic field within the passively shielded enclosure; a wearable MEG measurement device including optically pumped magnetometers (OPMs) and wearable active shield coils disposed adjacent the OPMs to reduce the ambient background magnetic field experienced by the OPMs; and active shield coils within the passively shielded enclosure and stationary relative to the passively shielded enclosure and wearable MEG measurement device, wherein active shield coils are configured to further reduce the ambient background magnetic field within the user area of the passively shielded enclosure.

In at least some embodiments, at least one of the active shield coils is configured for attachment to at least one of the walls of the passively shielded enclosure. In at least some embodiments, all of the active shield coils are configured for attachment to the walls of the passively shielded enclosure. In at least some embodiments, at least one of the active shield coils is configured for free-standing in the passively shielded enclosure.

In at least some embodiments, the shielding arrangement further includes an active shield controller coupleable to the active shield coils, wherein the active shield controller is configured to provide a plurality of independent channels with each of the active shield coils coupled to any one of the independent channels. In at least some embodiments, the active shield coils include at least thirty active shield coils.

In at least some embodiments, the plurality of walls includes a floor, a ceiling, and a first wall having an open doorway without a door for entering or exiting into the passively shielded enclosure, the shielding arrangement further including a vestibular wall extending from the first wall toward another of the walls to define, and at least partially separate, a vestibular area of the passively shielded enclosure adjacent the doorway and a user area of the passively shielded enclosure.

In at least some embodiments, the shielding arrangement further includes a mobile platform, wherein the passively shielded enclosure is mounted on the mobile platform. In at least some embodiments, the shielding arrangement further includes at least one sensing modality disposed in the passively shielded enclosure to monitor a position or orientation of the wearable MEG measurement device. In at least some embodiments, the shielding arrangement further includes an active shield controller coupleable to the active shield coils and to the at least one sensing modality and configured to alter generation of magnetic fields by the active shield coils in response to the monitored position or orientation of the wearable MEG measurement device.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
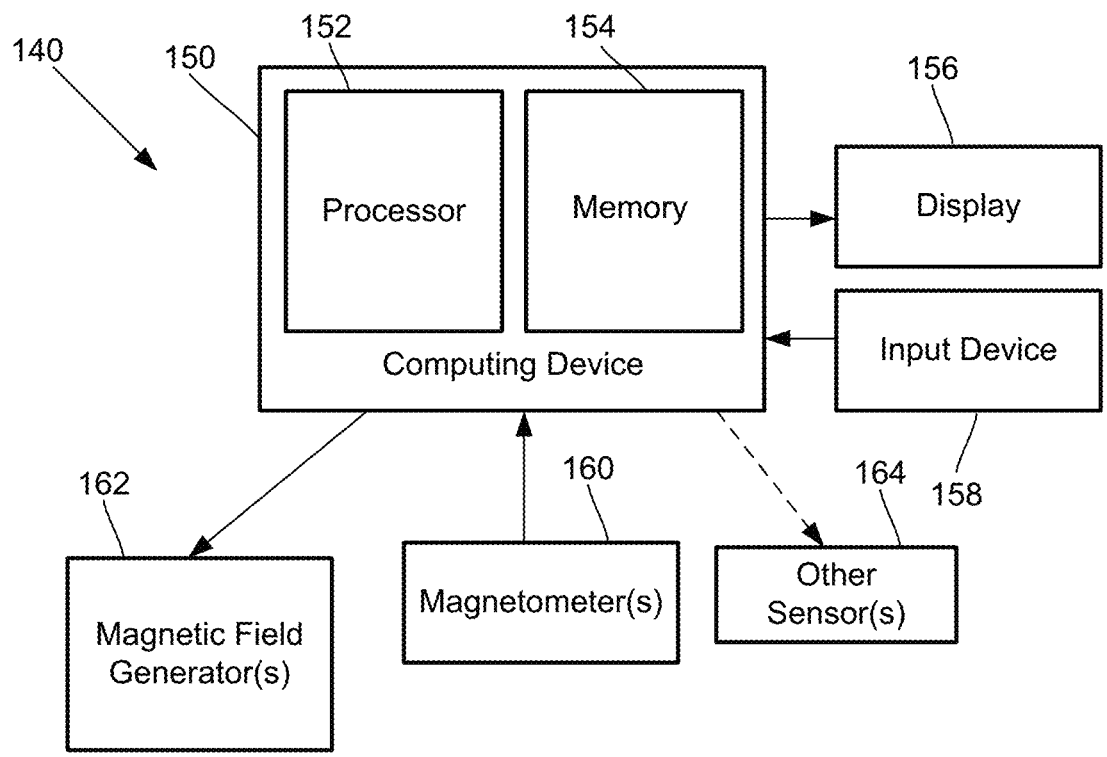
FIG. 1A is a schematic block diagram of one embodiment of a magnetic field measurement system, according to the invention.

The present disclosure is directed to the area of magnetic field measurement systems including systems for magnetoencephalography (MEG). The present disclosure is also directed to magnetic field measurement systems and methods for suppressing background or interfering magnetic fields. Although the present disclosure utilizes magnetoencephalography (MEG) to exemplify the OPMs, systems, and methods described herein, it will be understood that the OPMs, systems, and methods can be used in any other suitable application.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. This technology can also be applicable for uses outside biomedical sensing. In at least some embodiments, the system can be a wearable MEG system that can be used outside a magnetically shielded room. Examples of wearable MEG systems are described in U.S. Patent Application Publication No. 2020/0057115 and U.S. Provisional Patent Application Ser. No. 63/170,892, all of which are incorporated herein by reference in their entireties.

A magnetic field measurement system can utilize one or more magnetic field sensors. Magnetometers will be used herein as an example of magnetic field sensors, but other magnetic field sensors may also be used. FIG. 1A is a block diagram of components of one embodiment of a magnetic field measurement system 140. The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions such as instructions provided as part of a demixing engine 155 stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used.

The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems, such as MEG systems, or methods of making such systems or components for such systems are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; 2020/0341081; 2020/0381128; 2020/0400763; US 2021/0011094; 2021/0015385; 2021/0041512; 2021/0041513; and 2021/0063510; U.S. patent application Ser. No. 17/087,988, and U.S. Provisional Patent Applications Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/052,327; 63/076,015; 63/076,880; 63/080,248; 63/089,456; 63/135,364; 63/136,093; 63/136,415; 63/140,150; 63/158,700; 63/159,823; and 63/170,892, all of which are incorporated herein by reference in their entireties. The OPMs, OPM modules, and other system components described in these references can be used in the MEG and other magnetic field measurement systems and methods described herein.

Figure 1B:
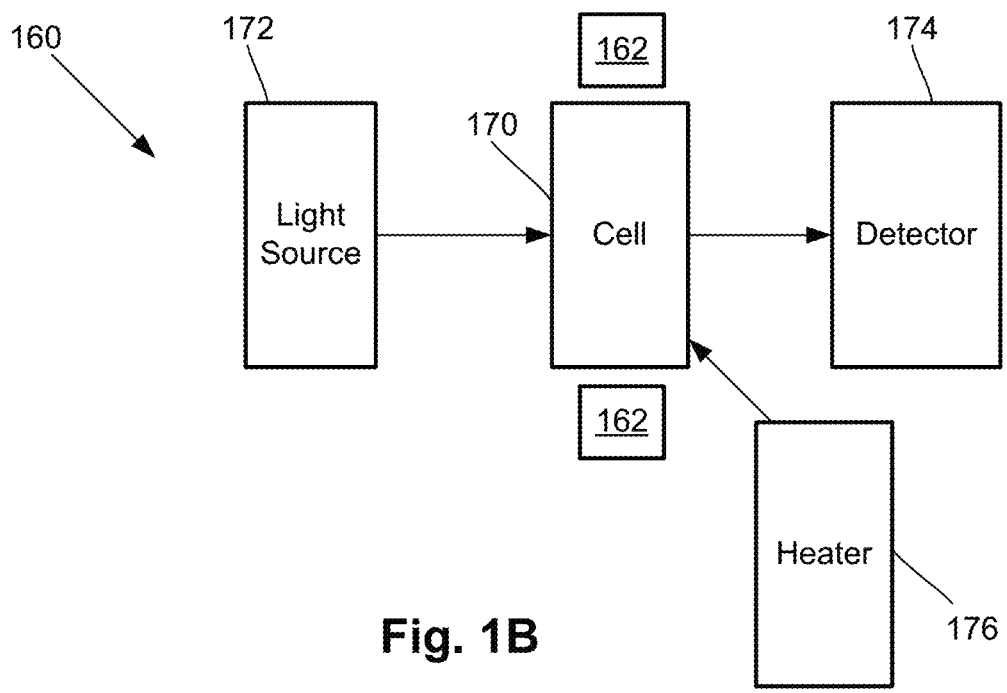
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell" or "vapor cell") such as an alkali metal vapor cell; a heating device 176 to heat the cell 170; a pump light source 172a; a probe light source 172b; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The pump and probe light sources 172a, 172b can each include, for example, a laser to, respectively, optically pump the alkali metal atoms and probe the vapor cell. The pump and probe light sources 172a, 172b may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
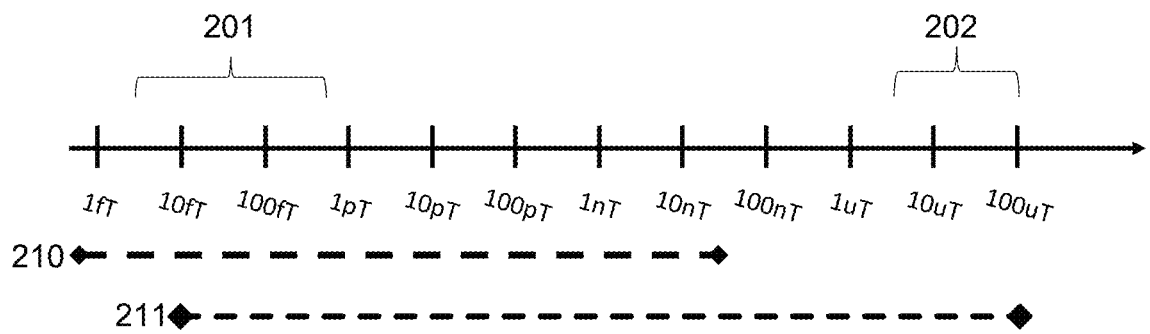
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 μT.

Magnetoencephalography (MEG) is the study of the magnetic fields generated by the living human brain. These measurements are conventionally performed using cryogenic superconducting quantum interference devices (SQUIDs) or optically pumped magnetometers (OPMs). MEG using SQUIDs may require unnatural user head motion constraints due to sensor insulation bulk.

OPMs attain sufficient sensitivity to acquire neural signals when operating in low ambient background magnetic fields. For the purposes of this disclosure, "low" indicates magnetic field strengths that are a fraction of the linewidth of the magnetic resonance of the OPM, which is typically in the 1 to tens of nanoTesla. The ordinary environmental ambient background magnetic field in human-relevant contexts on Earth is typically on the order of 50 microTesla at low frequency, and hundreds of nanoTesla root-mean-square (RMS) amplitude at the harmonics of the local powerline frequencies. This unmitigated ambient background magnetic field is large with respect to typical magnetic resonance linewidths of OPMs.

OPMs with optical pumping parameters selected for relatively small magnetic resonance linewidth (for example, embodied by low optical pumping laser power) may have limited dynamic range and typically utilize high magnetic field shielding (for example, a passively shielded room or an active shielding arrangement or a combination thereof) to reduce the ambient background magnetic field.

Conventional multi-user MEG in a passively shielded environment can be limited by the tendency for such environments to have only one region of best shielding (for example, the center of a passively shielded enclosure). MEG (either OPM or SQUID) in high passive-shielding environments may present an unnatural user experience due to uncomfortable passively shielded enclosures. For example, a passively shielded room may be relatively confined and have a relatively heavy or imposing door to maintain the passive shielding. Also, such systems may suffer from lack of manufacturability which may limit population-scale studies or use.

Conventional MEG using OPMs with no passive shielding may have stringent requirements for wearable active shielding components, which may reduce signal-to-noise because of high-current driver electronics noise. Such OPM arrangements may prevent or hinder dense full head coverage with OPMs by having large wearable coil systems to provide the needed active shielding. This can result in a relatively large fraction of volume unusable for OPM coverage within each module due to the active shielding. This can also result in limited nearest-neighbor OPM module packing density.

The systems and methods described herein can be used for magnetoencephalography (MEG) systems and other magnetic field measurement systems and methods. A MEG system will be used herein to describe the systems and methods, but it will be understood that the disclosed elements can also be used with other magnetic field measurement systems.

MEG systems, as described herein, can induce OPMs as described herein and in the cited references and can provide high fidelity neural recordings. The MEG system can include a comfortable, manufacturable magnetically shielded environment (MSE) with a combination of passive and active shield components. For example, the ambient background magnetic field can be attenuated by a stationary passively shielded enclosure. "Stationary" means stationary with respect to the user(s). In at least some embodiments, the ambient background magnetic field can be further attenuated by stationary active shield components, such as one or more arrays of coils fixed to, or disposed within, the interior of the passively shielded enclosure. The residual ambient background magnetic field can also be attenuated by wearable (for example, fixed with respect to the user) active shield components. In at least some embodiments, the optically pumped magnetometer (OPM) sensor modules include integrated wearable active shield components (for example, active shield coils and the magnetic field generators 162 of FIGS. 1A and 1B). The active shield coils can have an operating range sufficient to overlap with the lower bound of the residual ambient background magnetic field that penetrates the stationary passively shielded enclosure and reduced by the optional active shield fixed to, or disposed within, the passively shielded enclosure.

In at least some embodiments, OPM modules with active shield coils can provide a substantially uniform ambient background magnetic field across an ensemble of multiple OPMs within one OPM module. In at least some embodiments, using these passive and active shield components, the system can provide dense full head coverage with at least 100 to 1000 (or more) OPMs per user. In at least some embodiments, this dense full head coverage of OPMs with active shield coils can be in the form of a wearable device, such as a helmet, hood, cap, scarf, or other headgear or other shape conformable to a user's head.

The MEG system can also include other components, such as, OPM controller electronics to control operation of the OPMs; OPM laser(s) and fiber optic light delivery system(s) from the laser(s) to the OPMs; OPM detector electronics coupled to the OPMs to receive detected neural signals from the OPMs; a control computing device (for example, a desktop or laptop computer) that interfaces with the OPM controller electronics and OPM detector electronics; a helmet/mechanical support for the OPM modules (in a helmet or other headgear) to relieve user neck strain; active shield driver(s) to power and control the active shield components; and user interaction components (UIC) including, but not limited to, a controller, keyboard, screen, audio components, or head or eye movement tracking components including magnetic, gyroscopic and visual tracking components. The MEG system can also include software (for example, software residing on the control computer or other computing device) to record magnetic neural signals, environmental signals, user motion; to provide a user interface control; to provide stimulus inputs to a user; or any combination thereof. The references cited herein include examples of these components and software that can be utilized in the MEG systems (and other magnetic field measurement systems) described herein.

Figure 3:
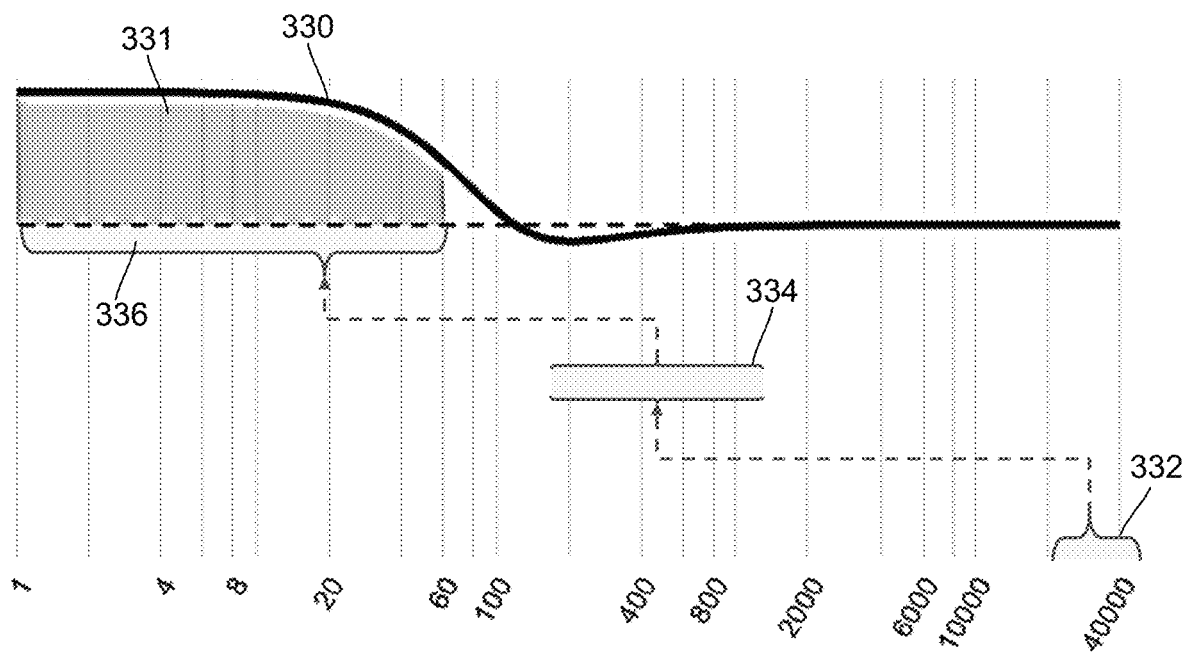
FIG. 3 shows a logarithmic graph of ambient background magnetic field and shows a range for operation of optically pumped magnetometers, as well as ranges for the ambient background magnetic field before and after reduction using passive and active shielding components, according to the invention.

FIG. 3 illustrates one embodiment of parameter interactions of a MEG or other magnetic field measurement system in relation to the total input magnetic field at the OPM. The horizontal axis indicates the magnitude of the magnetic field on a logarithmic scale.

A typical OPM magnetic resonance response 330 (such as a dispersive Lorentzian) has a limited operating domain 331 for best sensitivity, given by the width of the magnetic resonance. This domain is usually no greater than tens of nano-Tesla (nT). FIG. 3 illustrates a specific example of an OPM with a 60 nT domain maximum. In at least some embodiments, the shielding components of a MEG system reduce the total magnitude of the ambient background magnetic field to a value less than the maximum of this domain, and preferably much less than the domain maximum, to enable sufficient sensitivity for acquisition of faint signals such as those due to neural signals or other sources of biomagnetism. As described herein, this can be accomplished with a combination of passive and active shielding components.

Region 332 illustrates the magnitude of the ambient background magnetic field without any attenuation. In at least some embodiments, the ambient background magnetic field is attenuated from approximately 50,000 nT by a comfortable stationary passively shielded enclosure having a moderate shielding factor on the order of 200 to 250 to produce a resulting ambient background magnetic field in region 334, as described herein. In other embodiments, the shielding factor or a passively shielded enclosure can be in a range of 50 to 500. In at least some embodiments, achieving a higher passive shielding factor may be less desirable from the standpoint of user comfort because such passive shielding factors may require the use of a sealed door to achieve the passive shielding factor. Higher passive shielding factors may also degrade manufacturability which could limit population-scale studies or use.

Optionally, in a MEG or other magnetic field measurement system the residual unshielded fraction of the ambient background magnetic field can be further attenuated by a stationary active shield system. For example, in at least some embodiments active shield coils can be affixed (for example, as panels or other structural elements) to the interior walls of, or otherwise disposed or positioned within, the stationary passively shielded enclosure. In at least some embodiments, the MEG or other magnetic field measurement system can include a passively shielded enclosure with active shield coils in the form of panels to provide a substantial actively shielded open volume. In at least some embodiments, the active shield coils can be used to allow for user motion by shifting the region in which the ambient background magnetic field is most reduced as the user moves.

In at least some embodiments, the stationary active shield system can include an active shield control system to monitor the residual ambient background magnetic field in the passively shielded enclosure and attenuate the residual ambient background magnetic field within a target region inside the passively shielded enclosure. In at least some embodiments, the active shield control system can alter the magnetic fields generated by the active shield system to move the target region with the lowest residual ambient background magnetic field to, for example, follow movements of the user or the head of the user. In at least some embodiments, the stationary active shield system may be optionally enhanced by user-tracking feedback control that tracks the user's movement within the actively shielded volume inside the stationary passively shielded enclosure to maintain the wearable OPMs in a target region of reduced ambient background magnetic field of some usable volume that can move with the user.

The residual ambient background magnetic field can be further attenuated to a region 336 by a comfortable wearable active shield subsystem. In at least some embodiments, the active shield subsystem can facilitate user comfort with high performance by use of compact coils and low-noise electronics. In at least some embodiments, these are enabled by limiting the maximum domain of the operating range of the wearable active shield system to generating attenuating magnetic fields no greater than approximately 1000 nT.

In at least some embodiments, the OPM is operated in a large-magnetic-linewidth regime to increase the domain of operation to encompass the residual unshielded fraction of the ambient background magnetic field that passes through the passive and active shield subsystems. One method to attain large linewidth in an OPM includes operating with relatively high input light power, which causes power broadening of the intrinsic magnetic resonance. This method has the additional advantages of: 1) integrating well with the active and passive shield subsystems via lightweight, flexible optical-fiber tether to a distant high-power laser source while maintaining user comfort; and 2) increasing the magnetic resonance linewidth, without substantially degrading the OPM performance, in the domain where OPM noise is determined by the pump laser photon shot noise.

A MEG or other magnetic field measurement system, as described herein, can include a number of OPMs disposed in a wearable arrangement such as, for example, a helmet, hood, cap, scarf, or other headgear or other shape conformable to a user's head. In at least some embodiments, the OPM linear range or operating domain is at least 20 nT. In at least some embodiments, the number of OPMs in a wearable arrangement that can be placed on a user's head is at least 25, 32, 50, 64, 100, 128, 200, or more. In at least some embodiments, the active magnetic shield coils in a wearable arrangement can compensate for an ambient background magnetic field of at least 50 nT. In at least some embodiments, the residual ambient background magnetic field after reduction by passive shielding of a MEG system is in the range of 50 to 1000 nT. In at least some embodiments, the residual ambient background magnetic field around the user after reduction by the optional stationary active shield coils is no more than 50, 75, or 100 nT.

Figure 4:
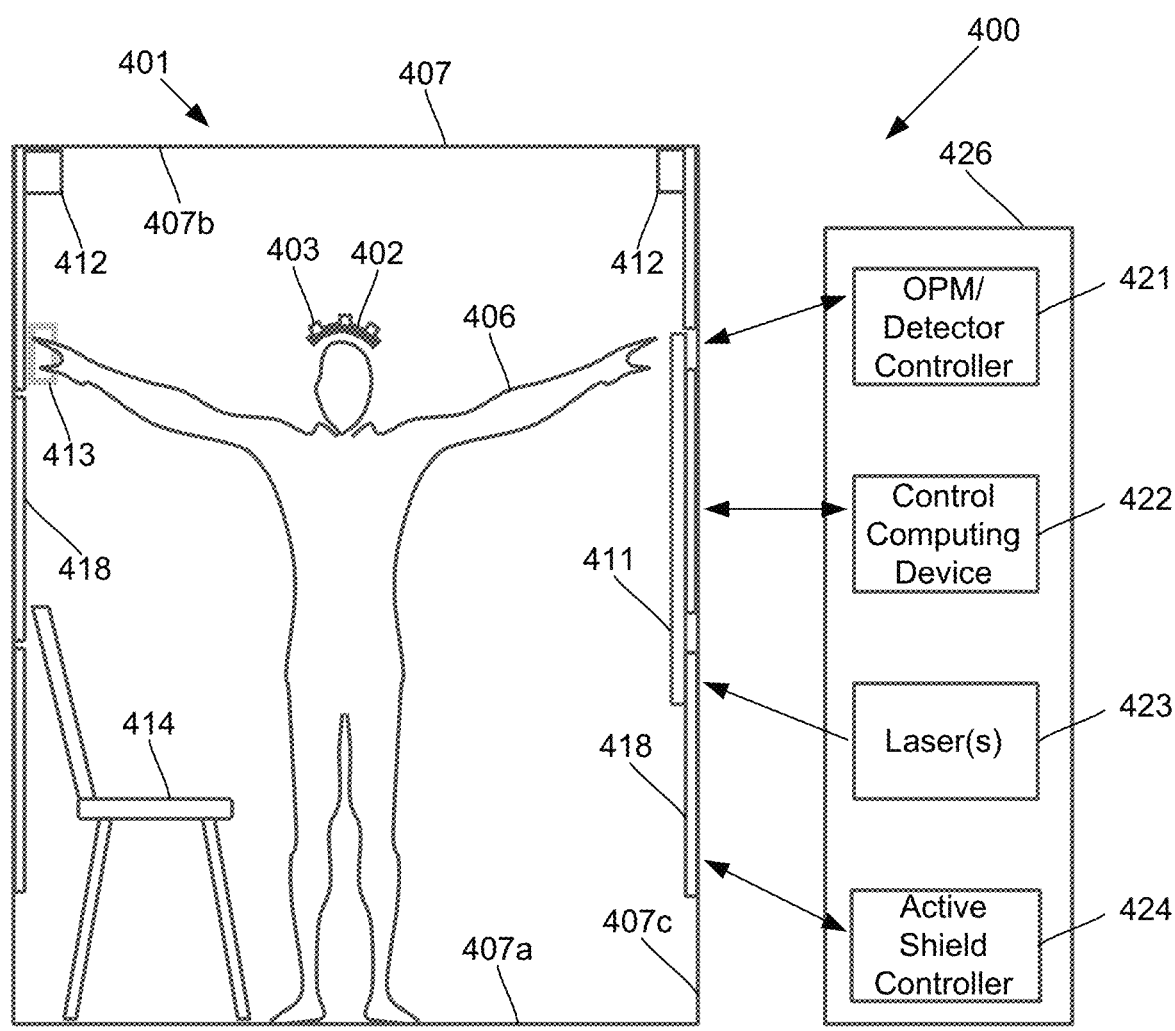
FIG. 4 is schematic side view of one embodiment of components of a magnetoencephalography (MEG) or other magnetic field measurement system including a passively shielded enclosure, according to the invention.

FIG. 4 illustrates a cross-sectional view of at least some components of one embodiment of a MEG or other magnetic field measurement system 400 with a shielding arrangement 401. The user 406 is wearing a helmet 402 populated with OPM modules 403. The user 406 is in a magnetically shielded environment (MSE) formed by the shielding arrangement 401 to reduce the ambient background magnetic field for operation of the OPM modules 403 and measurement of neural signals using the OPM modules. The shielding arrangement 401 can be, for example, a combination of passive shielding, for example, a passively shielded enclosure 407 (such as a passively shielded room), and optional active shielding for reduction of the residual ambient background magnetic field by, for example, active shield coils 418 (e.g., electromagnetic coils).

The passively shielded enclosure 407 can be made using passive shielding material, such as mu-metal or permalloy, or any other suitable material that reduces the ambient background magnetic field within the passively shielded enclosure. In at least some embodiments, the passively shielded enclosure 407 can be a room and can include a floor 407a, a ceiling 407b, and one or more vertical walls 407c extending from the floor to the ceiling. Each of the floor 407a, ceiling 407b, and vertical wall(s) 407c can include the passive shielding material.

Figure 5:
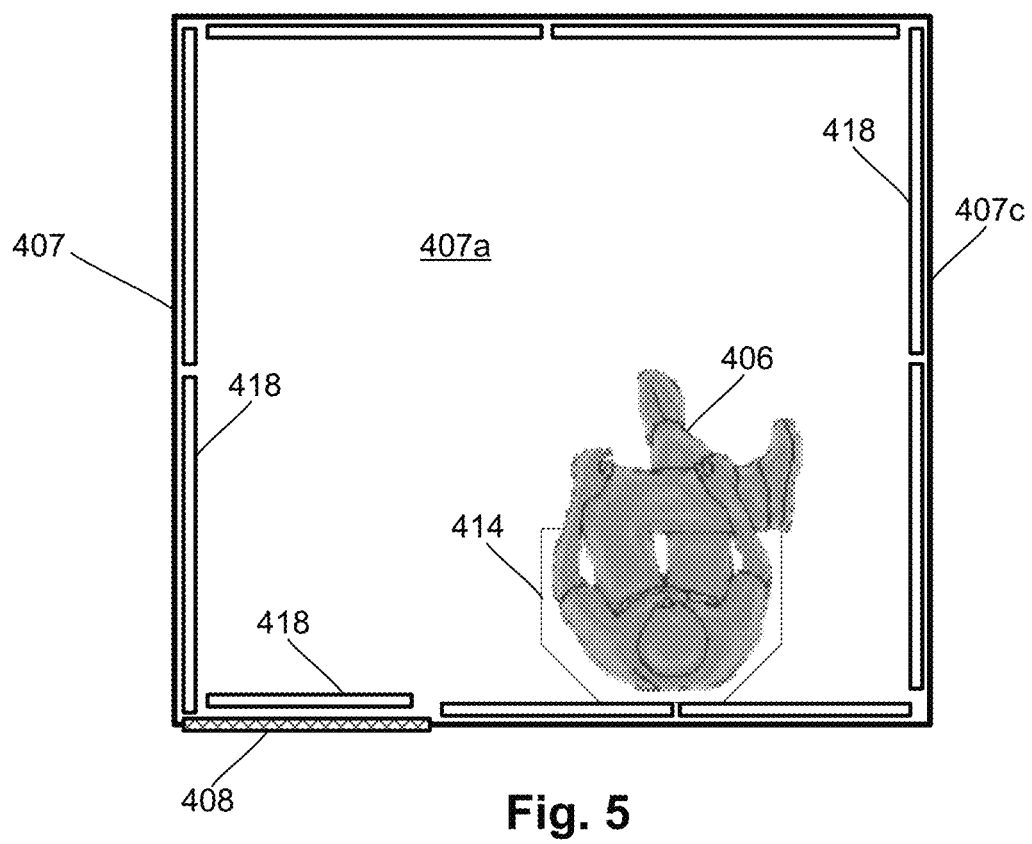
FIG. 5 is schematic plan view of one embodiment of a MEG or other magnetic field measurement system including a passively shielded enclosure with a shielded door, according to the invention.

FIG. 5 is a plan view of one embodiment of a passively shielded enclosure 407 in which a user 406 is seated on a chair 414. This passively shielded enclosure 407 includes a floor 407a, a ceiling (not shown), and multiple vertical walls 407c, as well as a door 408, one or more (or all) of which include the passive shielding material. In the illustrated embodiment, the optional active shield coils 418 are disposed on the vertical walls 407c and, optionally, the door 408. In at least some embodiments, active shield coils 418 may also be disposed on the floor 407a or ceiling (not shown) or both. In other embodiments, instead of disposing the active shield coils 418 on the vertical walls 407c or other portions of the passively shielded enclosure 407, some or all of the active shield coils can be disposed around the passively shielded enclosure. In at least some embodiments, one or more of the active shield coils 418 can be free-standing elements disposed in the passively shielded enclosure 407.

The passively shielded enclosure 407 of FIG. 5 may pose challenges for use. In at least some embodiments, the door 408 may be a weak region in the passive shielding. In other embodiments, the door 408 may be large, heavy, or otherwise imposing. The passively shielded enclosure 407 may also feel uncomfortable or claustrophobic to at least some individuals, particularly when the door is closed.

Figure 6:
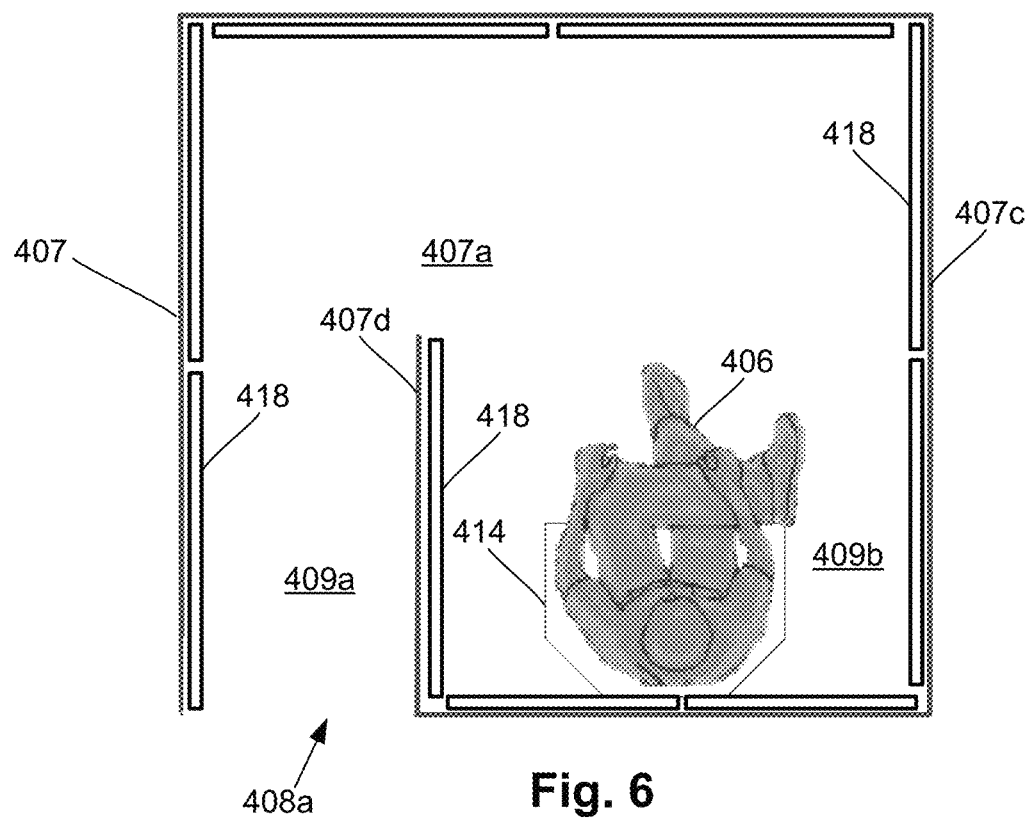
FIG. 6 is schematic plan view of one embodiment of a MEG or other magnetic field measurement system including a passively shielded enclosure with an open entryway, according to the invention.

FIG. 6 illustrates another embodiment of a passively shielded enclosure 407 with a user 406 seated in a chair. This passively shielded enclosure 407 includes a floor 407a, ceiling (not shown), and multiple vertical walls 407c, as well as a vestibular wall 407d, all of which include the passive shielding material. The vestibular wall 407d can spatially separate the space into a vestibular area 409a and a user area 409b. This passively shielded enclosure 407 does not include a door (although other embodiments may have a door), but rather has an open entryway 408a. In at least some embodiments, the vestibular wall 407d and vestibular area 409a remove the need for a shielded door. The vestibular wall 407d at least partially separates the user area 409b from the open entryway 408a. Removing the shielded door can greatly improve the user experience and feeling of openness but may reduce the shielding factor of the passively shielded enclosure 407. The presence of an open entryway 408a, although separated from the user 406 by the vestibular wall 407d, may result in the passively shielded enclosure 407 feeling more comfortable or less claustrophobic for the user.

The vestibular wall 407d can extend from one of the vertical walls 407c toward another one of the vertical walls, as illustrated in FIG. 6. In at least some embodiments, the vestibular wall 407d can extend from floor 407a to ceiling (not shown). In other embodiments, the vestibular wall 407d may not extend all of the way to the floor 407a or the ceiling (not shown) or both.

The absence of a door to the passively shielded enclosure 407 and the use of the vestibular wall 407d and vestibular area 409a may make access (entry and exit) easier and more natural for a user or technical personnel. In at least some embodiments, compensation for reduced passive shielding due to the absence of the door can be achieved through the use of the vestibular wall 407d, which may reduce the ambient background magnetic field within the user area 409b of the passively shielded enclosure 407 which may be enhanced by the optional incorporation of passive shielding material in the vestibular wall. In at least some embodiments, further reduction can be achieved using the optional active shield coils 418 in the passively shielded enclosure and the active shield coils within the OPM modules 403.

In the illustrated embodiment, the optional active shield coils 418 are disposed on the vertical walls 407c and, optionally, the vestibular wall 407d. Passive shielding on the vestibular wall 407d or the active shield coils 418 (or both) can be used to compensate for the loss of passive shielding at the open entryway 408a. In at least some embodiments, active shield coils 418 may also be disposed on the floor 407a or ceiling (not shown) or both. In other embodiments, instead of disposing the active shield coils 418 on the vertical walls 407c, vestibular wall 407d, or other parts of the passively shielded enclosure 407, some or all of the active shield coils can be disposed around the passively shielded enclosure. In at least some embodiments, one or more of the active shield coils 418 can be free-standing elements disposed in the passively shielded enclosure 407.

Returning to FIG. 4, in at least some embodiments, an active shield controller 424 is coupled to the active shield coils 418 to control the reduction in the ambient background magnetic field within the passively shielded enclosure 407. In at least some embodiments, the active shield controller 424 has multiple channels with one or more of the active shield coils 418 coupled to each channel. For example, there can be two, three, four, six, eight, ten, twelve, 15, 20, 25, or more channels and two, four, six, eight, ten, twelve, 15, 20, 25, 30, 32, 40, 50, 60, 64, 70, 80, 90, 100, 120, 128, or more active shield coils. In at least some embodiments, two or more of the channels are independently operable meaning that operation of the independent channels does not depend on the other channels. In at least some embodiments, the active shield coils 418 are conductive wire or conductive traces and may be mounted on a substrate, such as a printed circuit board substrate.

In at least some embodiments, user movement is monitored through one or more (for example, a combination of two or more) sensing modalities including, but not limited to, optical tracking 412, magnetic tracking implemented through the OPM modules 403 or other magnetic tracking units, inertial tracking, or ultrasound tracking or the like. In at least some embodiments, the sensing modalities may also be used to track the pose (position and orientation) of the helmet 402 and OPM modules 403. Depending on the task the user is asked to perform or engage in, the user may be free standing, seated in a chair 414, or sleeping. Examples of sensing modalities systems, as used in the magnetically shielded environments described herein, or methods of using such systems, are described more fully in U.S. Provisional Patent Application Ser. No. 63/052,327, which is incorporated herein by reference in its entirety.

In at least some embodiments, as the user moves (or the user's head moves), the active shield controller 424 alters the magnetic fields generated by the active shield coils 418 to control the reduction in the ambient background magnetic field around the helmet 402 and OPM modules 403. In at least some embodiments, the residual ambient background magnetic field after reduction using the active shield coils 418 is not uniform within the passively shielded enclosure 407, but instead has a lowest residual ambient background magnetic field region that can be shifted or moved, using the active shield controller 424 and in response to the detection of user movement by the one or more sensing modalities, to remain at or near the helmet 402 and OPM modules 403.

To attain sufficient shielding factor to operate OPMs at biomagnetism-capable sensitivities, passive shielding with relatively high shielding factor, typically greater than 5000, is used. Another approach is to use active shielding. The MEG or other magnetic field measurement system disclosed herein uses both, with reduced requirements on the shielding factor from either passive or active shielding, in concert with a relatively large magnetic linewidth provided by suitable choice of optical pumping parameters in the OPM module. The combination of these parameters can provide a MEG or other magnetic field measurement system for natural user experiences, with manufacturability advantages that enable population-level studies. In at least some embodiments, the passive shielding factor requirements can be on the order of 200 to 300. For example, this passive shielding factor can allow for a door-free, single-layer mu-metal environment. In at least some embodiments, the active shielding currents can be achieved using low power electronics, on the order of 100 s of mA, and therefore the active field magnitudes are similarly achieved. This allows for low-cost, manufacturable, compact coils with low-noise current drivers. The optical pumping parameters can be attained by high-power laser sources, which are remote with respect to the OPMs and coupled optically by flexible, lightweight fiber optic lines.

In at least some embodiments, the MEG or other magnetic field measurement system allows for user movement, accessibility (no locking hinged-door required), and peripheral support by combining open-shielding, high dynamic range OPMs, and sophisticated control all in a single system. The user can move freely and, at least in some embodiments, the user's motions are tracked by visual tracking software, which is digitized, saved, and time synced with the brain signal data. In at least some embodiments, the user's motions are fed back into the control system to (for example, constantly or periodically) adjust the active shielding to reduce the ambient background magnetic field to the operational range of the OPMs at the location of the user.

Figure 7:
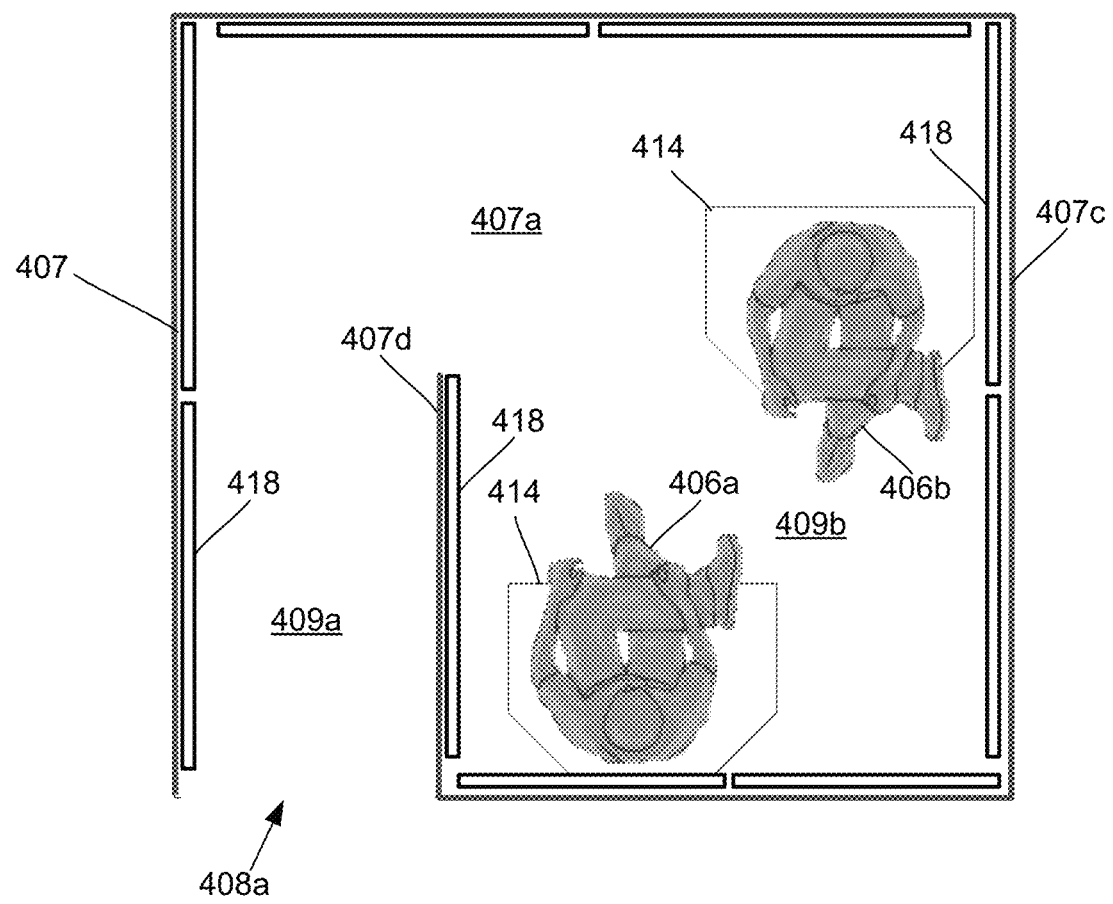
FIG. 7 is schematic plan view of one embodiment of a MEG or other magnetic field measurement system including a passively shielded enclosure with an open entryway for multiple users, according to the invention.

FIG. 7 is a top view of an embodiment of a passively shielded enclosure 407 with an open entryway 408*a* for a multi-user (for example, users 406*a*, 406*b*) MEG or other magnetic field measurement system.

Figure 8:
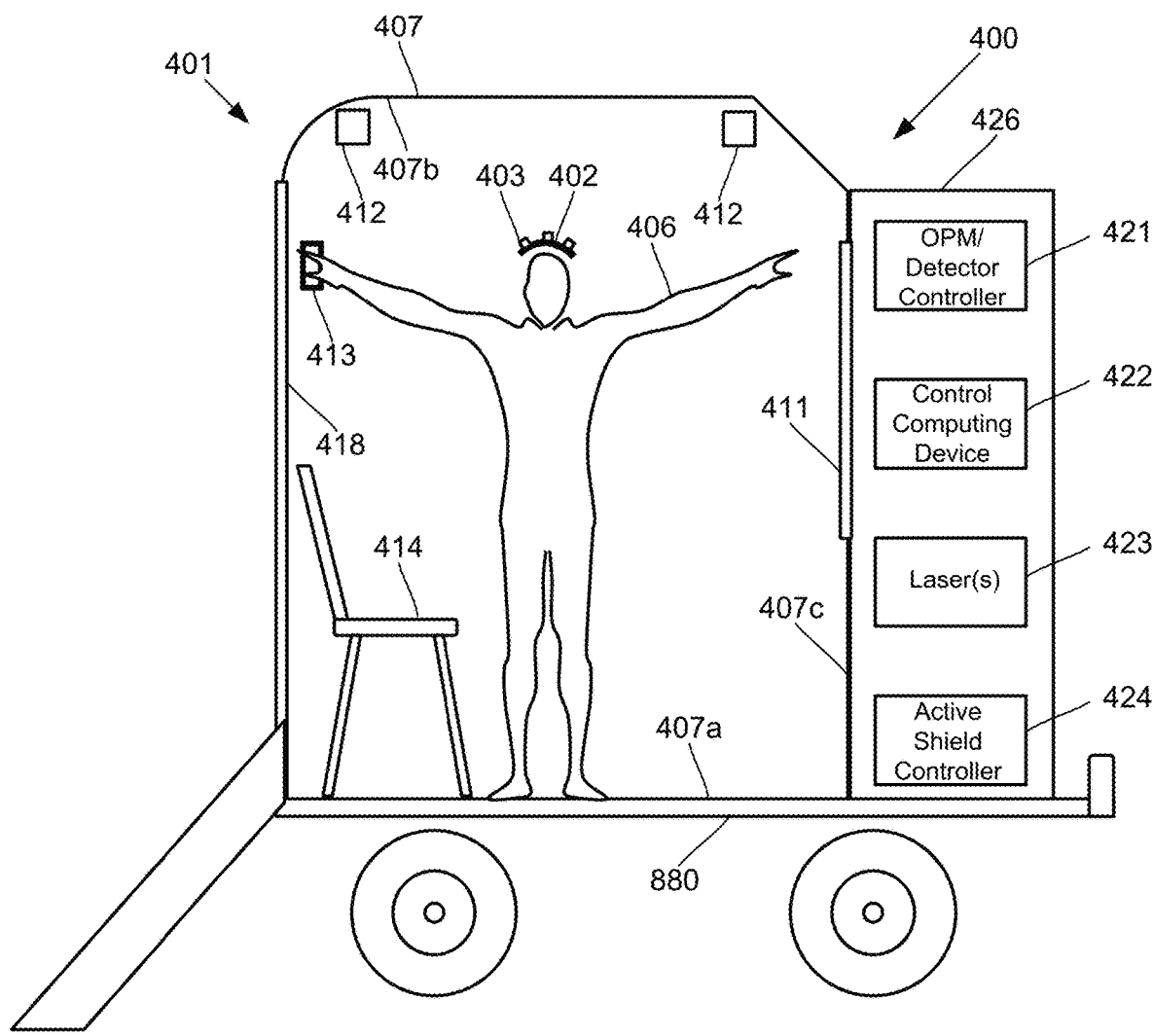
FIG. 8 is schematic side view of one embodiment of components of a MEG or other magnetic field measurement system including a passively shielded enclosure on a mobile platform, according to the invention.

FIG. 8 illustrates one embodiment of a mobile MEG or other magnetic field measurement system by mounting the passively shielded enclosure 407 (with or without a shield door 408) on a mobile platform 880 that could be any of, but not limited to, a trailer, shipping container, train car, airplane, watercraft, van, recreational vehicle, or the like. The mobile MEG system described herein can be easily moved from location to location, as necessary.

Returning to FIG. 4, in at least some embodiments, the user 406 can experience audio/visual stimulus from a screen or monitor 411 with or without sound generation capability. The MEG or other magnetic field measurement system can use the measured neural signals to provide feedback based on the audio/visual stimulus. Alternatively or additionally, the MEG or other magnetic field measurement system can also include one or more peripheral input devices 413 to provide feedback based on the audio/visual stimulus through one or more of the following: spoken response, movement, touch, or any other suitable mechanism. Examples of peripheral input devices include, but are not limited to, microphones, joysticks, hand-held controllers or the like, a mouse, buttons, cameras (for example, to detect eye motion, gaze direction, blinking, facial expression, hand or limb movement, or the like or any combination thereof), biometric devices (for example, to detect heart rate, respiration rate, skin conductivity, or the like or any combination thereof), or the like or any combination thereof. In at least some embodiments, the large dynamic range of the OPMs allows for the use of peripheral devices 413 which may have an associated active magnetic field due to electrical currents in the peripheral device or passive fields due to ferromagnetic materials such as nickel or iron.

In at least some embodiments, the MEG system 400 can include one or more exterior equipment cabinets 420 that provide storage for one or more of a system controller 421, a system computer 422, lasers 423, or the active shield controller 424. Examples of the components can be found in the references cited above and incorporated herein by reference in their entireties.

Figure 9:
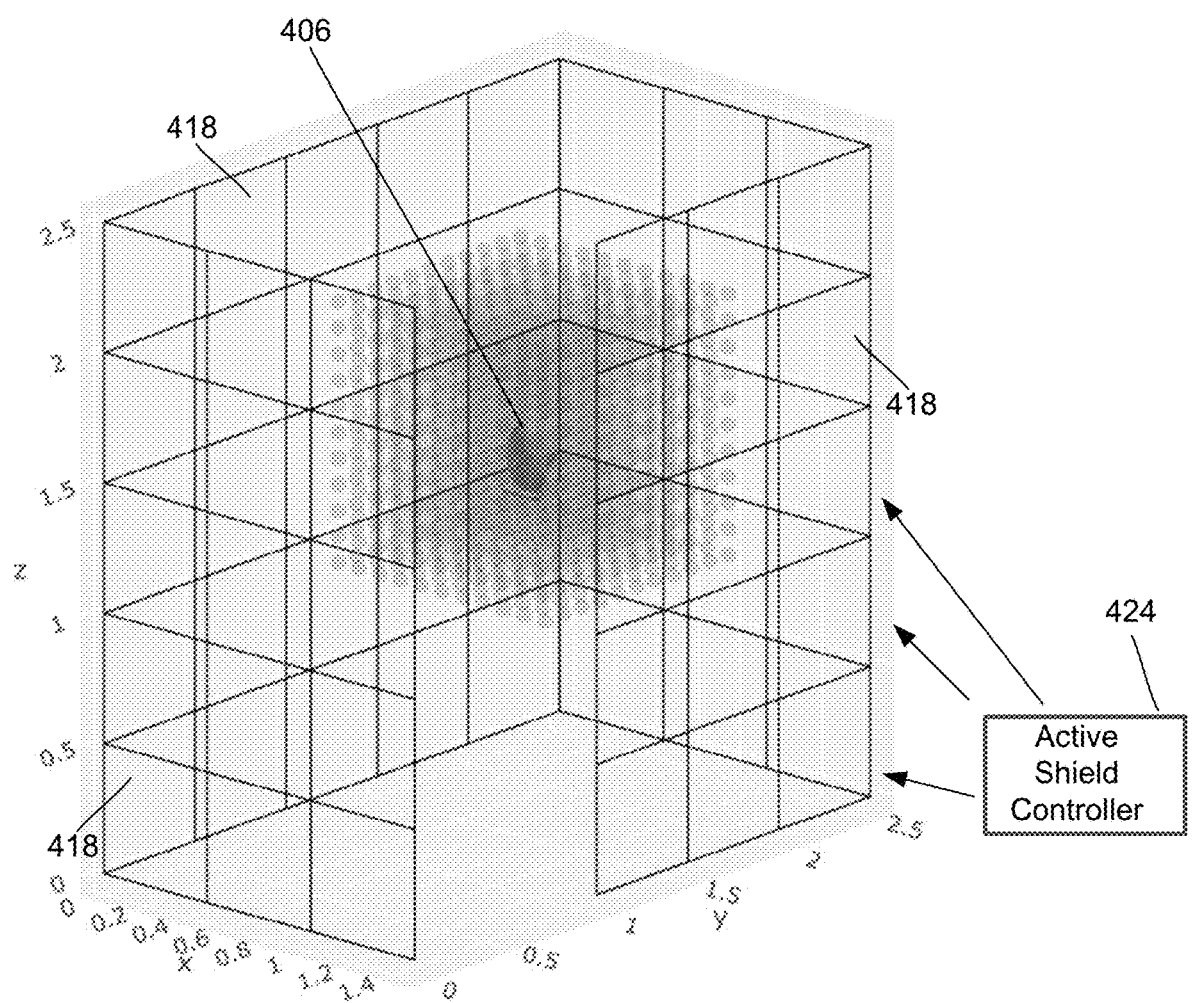
FIG. 9 is an illustration of an array of active shield coils with a user within the array, according to the invention.

FIG. 9 illustrates one embodiment of the active shield coils. In this configuration a quantity of seventy (70) shield coils 418 are shown as boxes. In other embodiments, there can be more or fewer shield coils including, but not limited to, 30, 32, 40, 50, 60, 64, 70, 80, 90, 100, 120, or 128 or more shield coils. In at least some embodiments, each of the shield coils 418 corresponds to a different independent channel, although in some embodiments, each channel might be coupled to two, three, four, or more shield coils. The shield coils 418 are 50 cm×50 cm square loops placed on the four vertical walls closest to the user 406, but not on the floor or ceiling or in the vestibule. This configuration can generate a large zero-field region 500 where a residual ambient background magnetic field of 300 µT can be reduced to less 57 nT. In at least some embodiments, if each of the shield coils 418 is 10 loops then the maximum current to achieve this is 190 mA. The active shield controller 424 generates the control signals for each of the shield coils.

The MEG or other magnetic field measurement systems and methods described herein can use one or more of the following: a door-free stationary passive shielded environment; an optional stationary active compensation coil array with, in at least some embodiments, 10 or more independent control channels; magnetic user tracking; large dynamic range (i.e., large magnetic linewidth) OPMs, for example, larger than 20 nT; a modular wearable active shielding system; arrays of OPMs within each active shielding module; or integrated screen(s), speaker(s), or peripherals or any combination thereof. In at least some embodiments, the system can be fully enclosed and optionally can be transported as a single unit and may include wheels (for example, a trailer). In at least some embodiments, the system can include an optical user tracking system, an optical user pose identification system, or the like or any combination thereof.

In at least some embodiments, the favorable manufacturability and low cost of the disclosed simple stationary passive shield arrangement of the MEG systems described above can better allow for population-level studies as compared to the current state-of-the-art MEG systems.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A shielding arrangement for a magnetoencephalography (MEG) system comprising a MEG measurement device, the shielding arrangement comprising:
   a passively shielded enclosure comprising a plurality of walls defining the passively shielded enclosure, each of the plurality of walls comprising passive magnetic shielding material to reduce an ambient background magnetic field within the passively shielded enclosure, wherein the plurality of walls comprises a floor, a ceiling, and a first vertical wall having an open doorway without a door for entering or exiting into the passively shielded enclosure;
   a vestibular wall extending from the first vertical wall to define, and at least partially separate, a vestibular area of the passively shielded enclosure adjacent the doorway and a user area of the passively shielded enclosure;
   a plurality of active shield coils distributed within the passively shielded enclosure and configured to further reduce the ambient background magnetic field within the user area of the passively shielded enclosure;
   at least one sensing modality disposed in the passively shielded enclosure to monitor a position or orientation of the MEG measurement device within the passively shielded enclosure; and
   an active shield controller coupleable to the active shield coils and to the at least one sensing modality and configured to alter generation of magnetic fields by the active shield coils in response to the monitored position or orientation of the MEG measurement device.

2. The shielding arrangement of claim 1, wherein at least one of the active shield coils is configured for attachment to at least one of the walls of the passively shielded enclosure.

3. The shielding arrangement of claim 1, wherein all of the active shield coils are configured for attachment to the walls of the passively shielded enclosure.

4. The shielding arrangement of claim 1, wherein at least one of the active shield coils is configured for free-standing in the passively shielded enclosure.

5. The shielding arrangement of claim 1, wherein the plurality of walls comprises a plurality of vertical walls including the first vertical wall, wherein the active shield coils are configured for attachment to the vertical walls.

6. The shielding arrangement of claim 1, wherein the active shield controller is configured to provide a plurality of independent channels with each of the active shield coils coupled to any one of the independent channels.

7. The shielding arrangement of claim 1, wherein the plurality of active shield coils comprises at least thirty active shield coils.

8. The shielding arrangement of claim 1, wherein the vestibular wall extends between the floor and the ceiling.

9. The shielding arrangement of claim 1, wherein the vestibular wall extends at least halfway between the first vertical wall and another of the walls.

10. The shielding arrangement of claim 1, further comprising a mobile platform, wherein the passively shielded enclosure is mounted on the mobile platform.

11. A magnetoencephalography (MEG) system, comprising:
    a passively shielded enclosure comprising a plurality of walls defining the passively shielded enclosure, each of the plurality of walls comprising passive magnetic shielding material to reduce an ambient background magnetic field within the passively shielded enclosure;
    a wearable MEG measurement device comprising a plurality of optically pumped magnetometers (OPMs) and a plurality of wearable active shield coils disposed adjacent the OPMs to reduce the ambient background magnetic field experienced by the OPMs;
    a plurality of stationary active shield coils within the passively shielded enclosure and stationary relative to the passively shielded enclosure and the wearable MEG measurement device, wherein the plurality of stationary active shield coils are configured to further reduce the ambient background magnetic field within a user area of the passively shielded enclosure;
    at least one sensing modality disposed in the passively shielded enclosure to monitor a position or orientation of the wearable MEG measurement device; and
    an active shield controller coupleable to the stationary active shield coils and the at least one sensing modality and configured to alter generation of magnetic fields by the stationary active shield coils in response to the monitored position or orientation of the wearable MEG measurement device.

12. The MEG system of claim 11, wherein at least one of the stationary active shield coils is configured for attachment to at least one of the walls of the passively shielded enclosure.

13. The MEG system of claim 11, wherein all of the stationary active shield coils are configured for attachment to the walls of the passively shielded enclosure.

14. The MEG system of claim 11, wherein at least one of the stationary active shield coils is configured for free-standing in the passively shielded enclosure.

15. The MEG system of claim 11, wherein the active shield controller is configured to provide a plurality of independent channels with each of the stationary active shield coils coupled to any one of the independent channels.

16. The MEG system of claim 11, wherein the plurality of stationary active shield coils comprises at least thirty of the stationary active shield coils.

17. The MEG system of claim 11, wherein the plurality of walls comprises a floor, a ceiling, and a first wall having an open doorway without a door for entering or exiting into the passively shielded enclosure, the passively shielded enclosure further comprising a vestibular wall extending from the first wall toward another of the walls to define, and at least partially separate, a vestibular area of the passively shielded enclosure adjacent the doorway and a user area of the passively shielded enclosure.

18. The MEG system of claim 11, further comprising a mobile platform, wherein the passively shielded enclosure is mounted on the mobile platform.

\* \* \* \* \*